United States Patent
Kershman et al.

(10) Patent No.: US 11,033,485 B1
(45) Date of Patent: Jun. 15, 2021

(54) DENTAL CARE SYSTEM CONTAINING ANTI-TARTAR AND ANTI-PLAQUE ACTIVES

(71) Applicant: Shear Kershman Laboratories, Inc., Chesterfield, MO (US)

(72) Inventors: Alvin Kershman, Chesterfield, MO (US); Jeff L Shear, Bonita Springs, FL (US)

(*) Notice: Subject to any disclaimer, the term of this patent is extended or adjusted under 35 U.S.C. 154(b) by 0 days.

(21) Appl. No.: 15/931,239

(22) Filed: May 13, 2020

Related U.S. Application Data

(60) Provisional application No. 62/848,614, filed on May 16, 2019.

(51) Int. Cl.
| | |
|---|---|
| *A61K 8/9789* | (2017.01) |
| *A61K 8/92* | (2006.01) |
| *A61K 8/06* | (2006.01) |
| *A61Q 11/00* | (2006.01) |
| *A61K 8/34* | (2006.01) |

(52) U.S. Cl.
CPC ............ *A61K 8/9789* (2017.08); *A61K 8/062* (2013.01); *A61K 8/345* (2013.01); *A61K 8/92* (2013.01); *A61Q 11/00* (2013.01); *A61K 2800/30* (2013.01); *A61K 2800/805* (2013.01); *A61K 2800/92* (2013.01)

(58) Field of Classification Search
CPC . A61K 33/30; A61K 8/46; A61K 8/72; A61Q 11/00
USPC .......................................................... 424/49
See application file for complete search history.

(56) References Cited

U.S. PATENT DOCUMENTS

| | | | |
|---|---|---|---|
| 4,145,412 A | 3/1979 | Landanyi | |
| 4,945,087 A | 7/1990 | Talwar | |
| 5,073,368 A | 12/1991 | Subramanian | |
| 5,298,238 A | 3/1994 | Hussein | |
| 5,811,079 A | 9/1998 | Yu | |
| 5,945,088 A | 8/1999 | Santi | |
| 8,586,102 B2 | 11/2013 | Rocker | |
| 8,758,729 B2 | 6/2014 | Nowak | |
| 9,173,941 B1 * | 11/2015 | Shear | A61K 31/573 |
| 2006/0045851 A1 | 3/2006 | Fitzgerald | |
| 2006/0275223 A1 * | 12/2006 | Burr | A61Q 11/00 424/49 |
| 2007/0140987 A1 * | 6/2007 | Doyle | A61K 33/34 424/49 |

* cited by examiner

*Primary Examiner* — Walter E Webb
(74) *Attorney, Agent, or Firm* — Linda L. Lewis

(57) ABSTRACT

A dental care system having from about 30 to 99 wt. % humectant; from about 1 to 50 wt. % water; from about 0.001 to 5.00 wt. % antiplaque and anti-tartar actives; from about 0 to 25 wt. % oil; from about 25 to 1 wt. % surfactant; and wherein the dental care system is hydrophobic and adheres to wet gums.

11 Claims, 2 Drawing Sheets

Initial after Application 30 min after Application 3 h after Application 2 h after Application 6 hours after application

DENTAL CARE SYSTEM CONTAINING ANTI-TARTAR AND ANTI-PLAQUE ACTIVES

CROSS-REFERENCE TO RELATED APPLICATIONS

This application claims the benefit of provisional patent application 62/848,614 filed May 16, 2019, which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to a dental care system for anti-tartar and anti-plaque actives and a method of using it. More specifically, the present invention relates to applying by rubbing on the gums a dental care system for anti-tartar and anti-plaque actives.

Related Art

*Sanguinaria canadensis*, Linne (family Papavaracease) is commonly known as Bloodroot, Redroot Puccoon, Teterwort, etc, is a perennial herb native to North America. The plant and its juices have been used for various purposes during the course of pre-history as well as written history. The plant has been generally used whole, either undried (fresh) or dried. The usual procedure is to powder the dried plant and mix it with a carrier. This folk remedy has been tried for such things as asthma, bronchitis, dysentery, ringworm, and a substantial list of other ailments.

U.S. Pat. No. 209,331, describes the use of Bloodroot, zinc chloride and kerosene oil in equal proportions for open sores. U.S. Pat. No. 433,257 describes a salve of pulverized bloodroot, Armenian bole, powdered rosin, lard and Stockholm tar in a treatment for piles. U.S. Pat. No. 2,344,830 describes the use of zinc chloride, stibnite and bloodroot to fix and outline diseased tissue for excising by surgery.

U.S. Pat. No. 4,145,412 discloses oral cleansing preparations and in particular to toothpaste using an extract of *Sanguinaria canadensis* as a portion of the preparation. The extract does not have the disagreeable properties of the powdered rhizome, and with other ingredients provides an oral cavity and tooth cleansing agent, a breath freshener and an oral cavity tissue conditioner. The extract from the bloodroot may be employed in amounts by weights, of from about 0.1% to about 50%, and preferably from about 1.00% to about 10.0% of the mixture, by weight. A toothpaste additive (Vinpoint additive) of the extract is prepared from the following:

| Raw Materials | Amount (g) | % by Weight |
|---|---|---|
| Vipont additive: | | |
| Glycerin | 758 | 75.8 |
| Water | 101 | 10.1 |
| Zinc chloride | 136 | 13.6 |
| Bloodroot Extract | 5 | 0.5 |

The Vinpoint additive is made with glycerin weighed into a vessel and heated to about 65° C. Zinc chloride is dissolved in deionized water, and this solution is filtered and added to the bloodroot extract and stirred. This forms a lumpy paste which is placed in a mixing bowl. The remainder of the paste is washed into the vessel with the warmed glycerin. The mixture is stirred until homogenous. The amount of zinc chloride is useful from 0.1-30% and preferably about 01-15% by weight.

A toothpaste is made with the bloodroot extract (Vinpoint) additive placed in a mixing bowl and sorbitol added. Polysorbate 80 (Tween® 80) with an HLB of 15 is added and the mixture is stirred. Tragacanth is added in small portions to avoid lumping and the mixture is stirred continuously during the addition. Mint flavoring is added and the mixture stirred until homogenous. At this point, saccharin and parabens are added with continued stirring. Anhydrous dicalcium phosphate is added in small portions with stirring. The dicalcium phosphate dihydrate is added in portions with stirring. Some portions of the water must be added along with the phosphate to maintain a good consistency for thorough mixing. The remaining water is added, and the mixture stirred to the desired consistency of toothpaste. A solution made from the paste has about a neutral pH. The amount of zinc chloride is useful in an amount of 0.1-30% by weight, and in the paste from about 0.1 to 3 weight percent.

| Raw Materials | Amount (g) | % by Weight | % by category |
|---|---|---|---|
| Vipont additive: | | | |
| Glycerin | 150.08 | 15.01 | |
| Water | 20.00 | 2.00 | |
| Zinc chloride | 26.93 | 2.69 | |
| Bloodroot Extract | 0.99 | 0.10 | |
| Sorbitol (70%) | 550 (385 sorbitol, 165 water) | 10.0 (7.0 sorbitol, 3.0 water) | 22.01 Total humectant |
| Polysorbate 80 | 100 | 2.0 | |
| Tragacanth | 105 | 2.1 | |
| Penick mint C-486 | 31.25 | 0.625 | |
| Sodium Saccharin | 15 | 0.3 | |
| Methylparaben | 7.5 | 0.15 | |
| Propylparaben | 0.75 | 0.015 | |
| Dicalcium Phosphate, anhydrous | 300 | 6.0 | |
| Dicalcium phosphate2H2O | 1100.5 | 22.01 | 27.01 Total water |

U.S. Pat. No. 4,145,412 fails to disclose the claimed system composition and the method of applying the system to the gums.

The use of mouthwashes to apply anti-tartar and anti-plaque actives to the oral cavity is well-known. The use of gels to apply actives to the gum is also known, but the method of rubbing the gel onto the gum to cause the gel to adhere to the gum (where the gel is not removed by rinsing and spitting) is not known nor disclosed in the art.

SUMMARY OF THE INVENTION

The present invention relates to a dental care system containing anti-tartar and anti-plaque actives made by combining an aqueous phase with anti-tartar and anti-plaque actives, water and at least one humectant with an oil phase. The at least one humectant is present in the aqueous phase in the range of from 1 to 99 wt. %, and the oil phase comprises at least one surfactant and optionally at least one oil in the range of about 0.001 to 25.0 wt. %. The surfactant is present in the oil phase in the range of from about 1 to 99.999 wt. %. The aqueous phase is added to the oil phase in a weight ratio of about 3:1 to 49:1. The aqueous phase is added to the oil phase using low to medium shear mixing to provide the dental care system. The dental care system is hydrophobic and adheres to the gums.

In a preferred embodiment, the oil phase comprises at least one oil and at least one surfactant, wherein the surfactant has a HLB of less than about 4.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
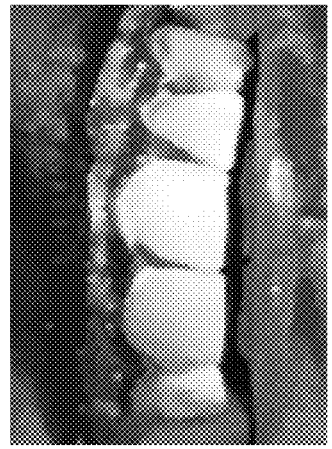
FIG. 1 is a collection of photographs showing the dental care system applied to the gums of a human.
Figure 1:
Figure 1:
Figure 1:
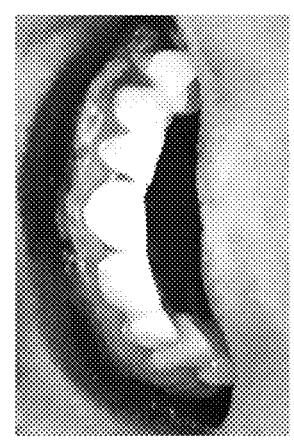

The following description of the preferred embodiment(s) is merely exemplary in nature and is in no way intended to limit the invention, its application, or uses.

The oil phase is prepared from a hydrophobic solution or mixture containing optionally at least one oil or petroleum distillate and at least one surfactant. The surfactant is preferably a non-water soluble surfactant having an HLB number of less than about 4, and includes emulsifiers. Examples of suitable surfactants include oleic acid, acetylated monoglycerides, glycerol dioleate, sorbitan tristearate, glycerol monoleate, acetylated monoglycerides and various combinations of these. A preferred surfactant is commercially sold as ATMOS® 300K, and is a combination of mono- and di-glycerides made from edible food sources and propylene glycol with an HLB of 2.8.

The surfactant is present in the oil phase in the amount of about 1.0 to 99.999%. The optional oil suitable for the oil phase is typically liquid or semi-solid at room temperature, and is compatible with the oral cavity. Such oils include essential oils, plant oils, such as vegetable oil, corn oil, canola oil, coconut oil, castor oil or olive oil, and animal fats such as tallow and lard. The oils include petroleum distillates, such as petrolatum and mineral oil. Mixtures of oils are also contemplated in the present invention. The oil phase is present in the system in the range of from about 0.1 to 25 wt. %. A preferred oil is pure extra virgin sesame expeller pressed oil. In a more preferred embodiment, the surfactant and the oil are present in the system in a weight ratio of about 20:1 to 1:1 surfactant to oil. In a more preferred embodiment, the surfactant and the oil are present in the system in a weight ratio of about 10:1 to 1:1 surfactant to oil.

The aqueous phase contains at least one humectant. Suitable humectants include, but are not limited to glycerin, lactic acid, polyols, propylene glycol, corn syrup, high fructose corn syrup (HFCS), including Cornsweet 55 and Cornsweet 42, and sorbitol. The preferred form of humectant is non-crystallizing liquid sorbitol (70 wt. % sorbitol in water). The at least one humectant is present in the aqueous phase from 1 to 99 wt. %. Preferably, the amount of humectant in the system is from about 45 to 99 wt. %. More preferably, the amount of humectant in the system is from about 60 to 99 wt. %.

In a preferred embodiment, the dental care system does not contain sorbitol and is sweetened with xylitol, which is more favorable to anti-caries properties.

Dental care systems of the present invention may also contain a fluoride source. Typical sources include soluble salts of the fluoride ion (e.g. sodium fluoride, potassium fluoride, stannous fluoride, stannous fluorozirconate) or, soluble salts of the mono fluorophosphate ion (e.g. sodium monofluorophosphate). The preferred fluoride source is sodium fluoride. The fluoride ion source should provide from about 50 ppm to about 2,500 ppm fluoride, preferably from about 250 ppm to about 1500 ppm for dentifrice and oral gel systems, and from about 50 ppm to about 250 ppm fluoride for oral rinses.

Antiplaque and anti-tartar actives are added to the aqueous phase of the system. *Sanguinaria canadensis*, Linne (family Papavaracease) products, commonly known as Bloodroot, Redroot, Puccoon, Teterwort, etc, is used as a source of anti-plaque active. Preferably, a powder of the dried plant is mixed with the aqueous phase. Additional antiplaque and anti-tartar actives include cetyl pyridinium chloride and related quaternary salts such as chlorhexidine; zinc salts such as zinc chloride and zinc sulfate monohydrate; stannous salts such as stannous chloride and stannous fluoride; and peroxides such as hydrogen peroxide and carbamide peroxide; sodium percarbonate; magnesium perphthalate; and sodium perborate. These antiplaque agents are generally present at levels ranging from about 0.01 weight % to about 5 weight %. A preferred range is from about 0.05 to about 1.5 weight %.

Preservatives such as a sorbate, a benzoate, chlorhexidine, chlorhexidine gluconate, chlorhexidine digluconate and breath fresheners such as a gluconate e.g., zinc gluconate, a sorbate e.g., potassium sorbate; and an antimicrobial e.g., a benzoate or a chlorhexidine can also be added.

Other additives suitable for the present invention include, but are not limited to colorings, flavorings and abrasives.

The claimed composition is typically prepared using a planetary or counter rotating type mixer having a rubber lined mixing bowl equipped with a wire whip stirring device. Preferably, the wire whip is rubber coated. The aqueous phase is blended at relatively low shear (30-600 rpm's) into the oil phase, continuously forming a total encapsulation of the aqueous solution droplets by the oil. This process is enhanced significantly by the oil wet-able properties of the rubber lining of the mixing bowl. Rubber coating of the wire whip device improves the rate of processing.

In an embodiment of the invention, the process of preparing the system is conducted in 2 steps:

Step 1 produces a seed batch for further processing. The initial seed batch is produced by adding a small volume of oil phase to the lined mixing chamber or bowl at a sufficient depth that the wire whip or mixing device touches the oil while rotating. The wire whip is then engaged at rate of about 30 to 100 rpm's. The aqueous phase is added at a rate approximately equivalent to the initial volume of the oil solution per minute. That is, if the initial volume of the oil phase is 20 mL, then the aqueous phase is added at a rate of about 20 mL per minute while being mixed in at 30 to 100 rpm's. Once, the desired weight ratio of aqueous phase to oil phase is reached (about 3:1 to 49:1), this initial process step is concluded.

Step 2 begins with the seed batch of Step 1, at the desired final weight ratio of aqueous phase to oil phase. The volume of seed material needed for Step 2 is to about 5-20 volume % of the final mixing chamber volume. The mixing whip or equivalent stirring and folding device are engaged at a speed of about 50 to 600 rpm's. The oil and water phases are added separately and simultaneously to the starter batch at a ratio equal to that contained in the seed batch. The rate of adding the two separate solutions is about 1 to 5% of the mixing chamber capacity per minute. As the mixing bowl or chamber fills, excess liquid may be removed continuously without halting the process. Alternatively, the process can be halted for partial or entire contents removal. Once the process is halted and a portion of the contents removed, the retained material can be held for an extended period of time. Because coating of and encapsulation of the aqueous phase is almost immediate, and materials are mixed at final required ratio in step 2, all product produced at any time during step 2 is ready to use.

A dental care system comprising:
- from about 45 to 99 wt. % humectant;
- from about 1 to 50 wt. % water;
- from about 0.001 to 5.00 wt. % antiplaque and anti-tartar actives;
- from about 0 to 25 wt. % oil;
- from about 25 to 1 wt. % surfactant;
- wherein the dental care system is hydrophobic and adheres to the gums.

An embodiment is shown in Example 1, below.

Example 1

TABLE 1

Method of Preparing the Dental Care System
Anti-Tarter/Anti-Plaque System

| Ingredient | Weight | % |
|---|---|---|
| Oil Phase | | |
| ATMOS 300K Surfactant | 40.50 | 13.50 |
| Pure Extra Virgin Sesame Expeller Pressed Oil | 3.00 | 1.00 |
| Nat Peppermint Flavor Oil Soluble | 1.50 | 0.50 |
| Aqueous Phase | | |
| Zinc Sulfate Monohydrate USP/FCC | 0.60 | 0.20 |
| Sorbitol Solution 70% USP | 204.00 | 68.00 |
| Bloodroot Powder (Sanguinaria Canadensis) | 3.00 | 1.00 |
| Purified water (Distilled) | 45.60 | 15.20 |
| Chlorhexidine Digluconate 20% Aqueous Solution | 1.80 | 0.60 |
| Total | 300.00 | 100.0 |

A. Preparing Oil Phase (15.0 wt. % of Final System)
1. Warm extra virgin sesame expeller pressed oil and peppermint oil to 26.7° C.
2. Add ATMOS® 300K, mix well and set aside.

B. Preparing the Aqueous Phase (85.0 wt. % of the Final System)
1. Mix the sorbitol solution and water together. Mix well and warm to 43.33° C.
2. Add the zinc sulfate monohydrate, bloodroot powder and chlorhexidine digluconate solution and mix well.
3. Remove heat source.

C. Forming the Lotion
1. Using a 5 quart lab Hobart type planetary lab/kitchen mixer with a rubber or plastic lined wire whip and rubber or plastic lined bowl add 40 g of oil phase and stir on #2 setting.
2. Slowly add approx. 200-300 g aqueous phase with mixing.
3. Add remainder of the oil phase to the bowl. Slowly add remainder of the aqueous phase to the bowl with mixing. Scrape the sides of the bowl with a spatula to ensure thorough mixing.
4. Increase the speed to #4 for 10 minutes more, making sure to scrape the sides of the bowl occasionally. After 10 minutes, the lotion is prepared.

The dental care system of Example 1, Table 1, above, is a lotion that is viscous, pourable, non-water dispersible and has release properties for the actives. The lotion adheres to wet gums and remains in place for as much as three hours. In a preferred embodiment, the lotion remains in place on the gums for up to six hours. The actives are released to the gums and teeth.

The lotion of Example 1 was tested by applying to the wet gums of a human, as shown in FIG. 1. The lotion of Example 1 was applied by rubbing on with a finger. An UV light photograph was taken, showing the lotion present on the gums. After 30 min., 2 hours and 3 hours UV photographs were taken, showing the lotion remained adhered to the gums and present for more than three hours. It is critical that the lotion be rubbed onto the gums. If the lotion is merely placed in the mouth, it will not adhere, but will be rinsed out or swallowed to no effect. Rubbing it on the gums causes it to adhere to the tissue and be effective.

Figure 2:
FIG. 2 is a photograph showing the dental care system applied to the gums of dog.

In FIG. 2, the lotion of Example 1 was applied to the wet gums of a dog by rubbing with a cotton swab. Six hours after the application, a UV photograph was taken showing the presence of the lotion on the gums of the dog, a Maltese. The dog had a history of developing tartar at a rapid and repeatable rate. This required dental cleanings every 6-7 months. The lotion of Example 1 was weekly rubbed on her gums. Her teeth were clear of tartar and gingivitis for from 1 to 3 months. After discontinuing application of the lotion, she developed gingivitis within 2-3 weeks and significant tartar within 2 months.

Example 2

Batch Formula Calculator

| Ingredient | Weight | % |
|---|---|---|
| Oil Phase | | |
| ATMOS 300K Surfactant | 15.00 | 5.00% |
| citation 70 Mineral Oil | 9.00 | 3.00% |
| Eucalyptus Oil | 2.140 | 0.7132% |
| Methyl Salicylate | 1.396 | 0.4652% |
| Thymol NF Fine Powder, 80 Mesh | 1.489 | 0.4962% |
| Menthol (5-Methyl-2-[1-methyl-ethyl]cyclohexanol) | 0.977 | 0.3256% |
| Aqueous Phase | | |
| 62 D.E./44 Baume Corn Syrup Humectant | 135.00 | 45.00% |
| purified water (Distilled) | 135.00 | 45.00% |

The dental care system of Example 2, Table 2, above, is a lotion that is viscous, pourable, non-water dispersible and has release properties for the actives. The lotion adheres to wet gums and remains in place for as much as three hours.

In a preferred embodiment, the lotion remains in place on the gums for up to six hours. The actives are released to the gums and teeth.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

The invention claimed is:

1. A method of applying by rubbing on the wet gums of a human or an animal a dental care system containing anti-tartar and anti-plaque actives made by the process of combining:
   A) an aqueous phase comprising an aqueous solution or suspension containing at least one humectant, wherein the at least one humectant is present in the aqueous phase in the range of from about 0.1 to 99 wt. %, and at least one anti-tartar active and anti-plaque active;
   B) an oil phase comprising at least one surfactant, and optionally at least one oil, wherein the at least one surfactant is present in the oil phase in the range of from about 1 wt. % to 99.999 wt. %; wherein the aqueous phase is added to the oil phase in a weight ratio of about 3:1 to 49:1, and the aqueous phase is added to oil phase using low to medium shear mixing to provide the system;
   wherein the system adheres to the wet gums;
   wherein the system remains on the gums for at least three hours; and
   wherein the at least one surfactant consists of a combination of propylene glycol monoglyceride and propylene glycol diglyceride having an HLB of 2.8.

2. The dental care system of claim 1, wherein the system is free from sorbitol and contains xylitol.

3. The dental care system of claim 1, wherein the humectant is present in the system from about 68 wt. % to about 99 wt. %.

4. The dental care system of claim 1, wherein the humectant is present in the system from about 45 wt. % to about 99 wt. %.

5. The dental care system of claim 1, wherein the humectant is selected from the group consisting of glycerine, lactic acid, polyols, propylene glycol, high fructose corn syrup, and sorbitol.

6. The dental care system of claim 5, wherein the antiplaque and anti-tartar actives comprise *Sanguinaria canadensis* products and actives selected from the group consisting of cetyl pyridinium chloride, chlorhexidine, zinc chloride, zinc sulfate, stannous chloride, stannous fluoride, hydrogen peroxide, carbamide peroxide, sodium percarbonate, magnesium perphthalate, and sodium perborate.

7. The dental care system of claim 1, wherein the antiplaque and anti-tartar actives comprise *Sanguinaria canadensis* products.

8. A method of preparing a dental care system for applying to the gums of a human or animal comprising:
   A) mixing to form an aqueous phase at least one humectant and at least one antiplaque and anti-tartar active; wherein the at least one humectant is present in the aqueous phase in the range of from about 0.1 to 99 wt. %, and
   B) mixing to form an oil phase comprising at least one surfactant, and optionally at least one oil; wherein the at least one surfactant is present in the oil phase in the range of from about 1 to 99.999 wt. %; and
   C) adding the aqueous phase to the oil phase in a ratio of about 3:1 to 49:1 using low to medium shear mixing to provide the dental care system;
   wherein the dental care system adheres to wet gums;
   wherein the system remains on the gums for at least three hours; and
   wherein the at least one surfactant consists of a combination of propylene glycol monoglyceride and propylene glycol diglyceride having an HLB of 2.8.

9. The method of claim 8, wherein the humectant is selected from the group consisting of glycerine, lactic acid, polyols, propylene glycol, high fructose corn syrup, and sorbitol.

10. The method of claim 9, wherein the wherein the antiplaque and anti-tartar actives comprise *Sanguinaria canadensis* products.

11. The method of claim 10, wherein antiplaque and anti-tartar actives comprise *Sanguinaria canadensis* products and actives selected from the group consisting of cetyl pyridinium chloride, chlorhexidine, zinc chloride, zinc sulfate, stannous chloride, stannous fluoride, hydrogen peroxide, carbamide peroxide, sodium percarbonate, magnesium perphthalate, and sodium perborate.

* * * * *